United States Patent
Chatlynne et al.

(10) Patent No.: US 7,704,230 B2
(45) Date of Patent: Apr. 27, 2010

(54) PRESSURIZED FLUID RESERVOIR FOR AN INFUSION SYSTEM

(75) Inventors: Etan Chatlynne, Brooklyn, NY (US); Steven Nguyen, North Brunswick, NJ (US); Frank Cichocki, Easton, PA (US); David Lindh, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 1063 days.

(21) Appl. No.: 11/321,699

(22) Filed: Dec. 29, 2005

(65) Prior Publication Data

US 2007/0156103 A1    Jul. 5, 2007

(51) Int. Cl.
*A61M 5/00*    (2006.01)
*A61M 37/00*    (2006.01)

(52) U.S. Cl. ...................... 604/132; 604/257
(58) Field of Classification Search .................. 604/132
See application file for complete search history.

(56) References Cited

U.S. PATENT DOCUMENTS

| | | | |
|---|---|---|---|
| 2,348,176 A | 5/1944 | Gott et al. ...................... 99/174 |
| 3,468,308 A | 9/1969 | Bierman ..................... 128/214 |
| 3,908,652 A | 9/1975 | Weissinger ............. 128/214 E |
| 4,702,397 A | 10/1987 | Gortz ......................... 222/211 |
| 4,769,008 A | 9/1988 | Hessel ........................ 604/132 |
| 4,909,790 A | 3/1990 | Tsujikawa et al. ........... 604/132 |
| 4,968,301 A | 11/1990 | di Palma et al. ............. 604/132 |
| 5,080,652 A | 1/1992 | Sancoff et al. .............. 604/132 |
| 5,178,610 A * | 1/1993 | Tsujikawa et al. .......... 604/132 |
| 5,205,820 A * | 4/1993 | Kriesel ......................... 604/85 |
| 5,419,770 A | 5/1995 | Crass et al. ................. 604/123 |
| 5,573,646 A * | 11/1996 | Saito et al. ................... 204/266 |
| 5,776,103 A | 7/1998 | Kriesel et al. ............... 604/132 |
| 5,957,895 A | 9/1999 | Sage et al. ................... 604/181 |
| 6,024,724 A | 2/2000 | Lee ............................. 604/132 |
| 6,063,058 A * | 5/2000 | Sakamoto .................... 604/132 |
| 6,086,559 A | 7/2000 | Enk ............................ 604/121 |
| 6,086,560 A | 7/2000 | Kriesel ....................... 604/131 |
| 6,551,279 B1 | 4/2003 | Hyun ......................... 604/132 |

FOREIGN PATENT DOCUMENTS

| | | |
|---|---|---|
| EP | 0452912 A2 | 10/1991 |
| EP | 0464761 A1 | 1/1992 |
| EP | 0696460 A2 | 2/1996 |
| EP | 0933091 A2 | 8/1999 |
| GB | 1268569 | 3/1972 |
| WO | WO 96/04038 A1 | 2/1996 |
| WO | WO 99/30769 | 6/1999 |

* cited by examiner

*Primary Examiner*—Nicholas D Lucchesi
*Assistant Examiner*—Jason Flick

(57) ABSTRACT

A fluid reservoir for a medical infusion system includes an expandable elastomeric bladder defining a chamber for receiving and containing a volume of therapeutic substance and exerting pressure thereon to dispense the therapeutic substance from the bladder. The bladder has preferably a single port formed through the thickness thereof. A bi-directional valve is in fluid communication with the chamber of the elastomeric bladder and is used for filling the bladder chamber with the therapeutic substance and for connecting to a catheter assembly for dispensing the therapeutic substance to a patient undergoing treatment. The single port of the elastomeric bladder is connected to a medical grade flexible tubing, which is also connected to the bi-directional valve.

26 Claims, 5 Drawing Sheets

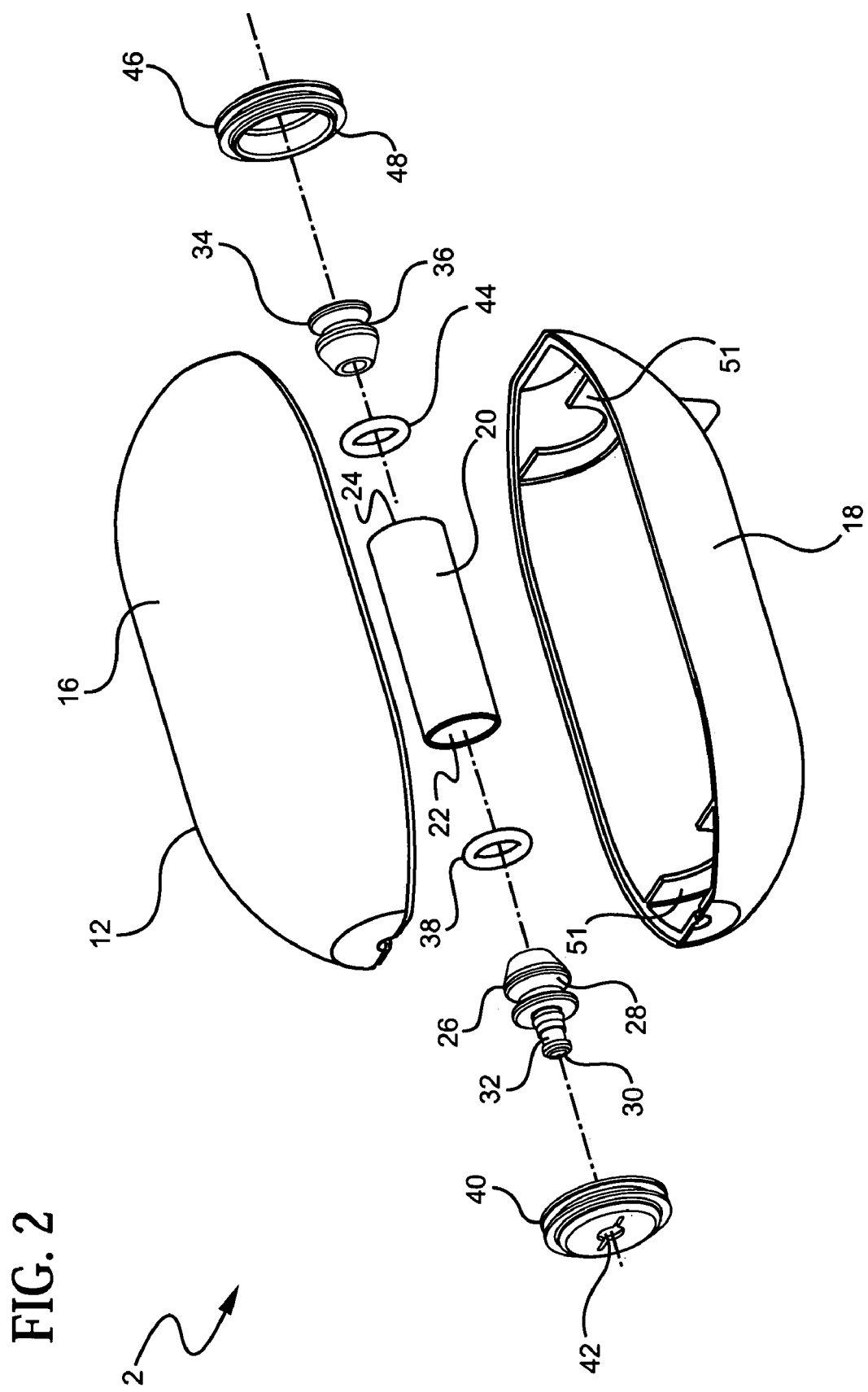

PRESSURIZED FLUID RESERVOIR FOR AN INFUSION SYSTEM

BACKGROUND OF THE INVENTION

1. Field of the Invention

The present invention generally relates to medical infusion systems for delivering therapeutic fluids to a patient, and more particularly relates to a fluid reservoir used as part of an infusion system or device for delivering such therapeutic agents into the body of a medical patient.

2. Description of the Prior Art

Many therapeutic fluids, for example, medicines, local anesthetics and the like, must be delivered to a patient for extended periods of time either subcutaneously or intravenously. The rate of the delivery of the therapeutic fluid must be well regulated to ensure a safe and efficacious treatment. Conventionally, this requires the attention of a medical professional who can monitor the fluid delivery on a regular basis.

Infusion pumps and catheters are frequently used in conjunction in an infusion system to deliver such therapeutic fluids to a patient for many purposes, for example, to alleviate postoperative pain, and chemotherapy. However, conventional systems do not address a number of significant functional or user interface issues.

Existing infusion devices require a series of preparation steps typically performed by a nurse or surgeon that may be easily confused by the user. For example, U.S. Pat. No. 4,769,008, which issued to Stephen R. Hessel, and U.S. Pat. No. 5,080,652, which issued to Gregory E. Sancoff et al., the disclosures of which are incorporated herein by reference, disclose infusion devices which require the user to connect a syringe to an input port and not to the output port after securing a clamp. If the syringe is attached to the incorrect end and pressure is applied, the device will malfunction, for example, an incorporated filter may be damaged (e.g., the filter media may pop). Furthermore, if the clamp is not activated properly, the device will not function properly, as fluid may be expelled from the device prematurely.

Many existing infusion devices require that the user perform difficult steps. For example, the aforementioned U.S. Pat. No. 5,080,652 to Sancoff et al. discloses an infusion device that requires the user to balance the device atop the filling syringe in a precarious position while the user applies a significant amount of hand force to the filling syringe, thereby creating a situation where the user may lose control of the device and the filling syringe. This may result in the device falling on the floor or in breaking the device. As another example, U.S. Pat. No. 4,909,790, which issued to Hajine Tsujakawa et al., the disclosure of which is incorporated herein by reference, describes a liquid infusion device having a stop-cock to regulate the flow into and out of a pressurized fluid reservoir, wherein the user must skillfully manipulate the stop-cock while retaining significant pressure on the filling syringe, thus requiring significant skill or strength on the part of the user to perform the steps required for using the infusion device.

Many other conventional infusion devices, such as most medical fluidic "needle-free" devices, utilize standard luer fittings for performing fluidic connections. Many infusion devices, for example, the On-Q™ PainBuster™ postoperative pain relief system manufactured by I-Flow Corporation of Lake Forest, Calif., and the Infusor™ infusion system manufactured by Baxter Healthcare Corporation of Round Lake, Ill., incorporate at least two luer fittings. The ubiquitous use of luer fittings has led to the accidental connection of unrelated medical devices, which may cause a patient further health problems or even death.

Many conventional infusion devices regulate flow commencement and termination using a simple plastic clamp, such as on the aforementioned I-Flow's On-Q™ PainBuster™ postoperative pain relief system, or a stop-cock, as disclosed in the aforementioned U.S. Pat. No. 4,909,790 to Tsujakawa et al. Often, a patient inadvertently ceases the delivery of a therapeutic fluid from the infusion device by accidentally closing the clamp, for example, by sitting on it. As a result, some surgeons and nurses have begun the practice of removing the clamp from the infusion device. But, many clamps are not designed to be removed, and this action could potentially damage the infusion device, for example, by cutting the device's tubing.

Other known infusion devices often must hold large volumes of fluid, sometimes up to one-half liter. Yet, it is the desire of patients who use the infusion devices that the infusion devices be unobtrusive, having a low profile and are "pocket-size". While some conventional infusion devices address this need, for example, the automatic injection device and reservoir disclosed in U.S. Pat. No. 5,957,895, which issued to Burton H. Sage et al., the disclosure of which is incorporated herein by reference, the inventors of the present device are unaware of any low profile devices that utilize an elastomeric bladder for the dual purpose of a) storing therapeutic fluids and b) providing system pressure.

Several currently marketed infusion devices incorporate elastomeric bladders that are generally affixed to a rigid structure using securing devices such as plastic or rubber rings, for example, the Accufuser™ disposable infuser manufactured by McKinley Medical, LLC of Wheat Ridge, Colo. or the aforementioned I-Flow's On-Q™ PainBuster™ postoperative pain relief system, or heat shrink tubing, for example; the aforementioned Baxter Infusor™ infusion system. In order to maintain structural integrity and to prevent the inflated bladder from displacing the securing device or to prevent the securing device from damaging the bladder, the bladders are provided with a very thick wall to allow for a deeper seat for the securing device. This thick wall requires that the user supply a higher pressure to inflate the bladder than would be necessary if an improved securing mechanism were utilized that did not require the use of a thick tube. Many users of existing devices have complained that these existing devices are difficult to inflate because of the strength required to impart inflation on the elastomeric bladder.

OBJECTS AND SUMMARY OF THE INVENTION

It is an object of the present invention to provide a pressurized fluid reservoir for an infusion system that has a number of advantages over conventional fluid reservoirs, including increased ease of use and increased design robustness.

It is another object of the present invention to provide a medical infusion device which minimizes the preparation steps required for using the device and minimizes the risk of performing each of the steps incorrectly.

It is a further object of the present invention to provide a medical infusion device for delivering a therapeutic fluid to a patient which does not require significant skill or strength to perform set-up steps and does not enable a disruption or failure of the device's function.

It is still another object of the present invention to provide a pressurized fluid reservoir connectable to an infusion device that reduces the risk that the user may connect an unrelated device to the reservoir of the present invention.

It is yet another object of the present invention to provide a medical infusion device which regulates a flow of a therapeutic substance to a patient, which device minimizes the likelihood of inadvertent flow manipulation.

It is yet a further object of the present invention to provide an infusion device having a flat-profile that incorporates an elastomeric bladder without altering the pressures generated by a typical non-low-profile infusion device.

It is another object of the present invention to provide an infusion device that incorporates an elastomeric bladder that is suitable for mid-use manipulation outside of a hospital by a non-medical professional.

It is a further object of the present invention to provide an infusion device that provides an ambulated patient with pre-filled reservoirs that may be used to replace an exhausted reservoir.

It is still a further object of the present invention to provide a medical infusion system which overcomes the inherent disadvantages of conventional infusion systems.

In accordance with one form of the present invention, a fluid reservoir for an infusion system includes an expandable elastomeric bladder which defines a chamber for receiving and containing a volume of therapeutic substance and exerting pressure thereon. The fluid reservoir also includes a bi-directional valve which is in fluid communication with the chamber of the elastomeric bladder. The bi-directional valve is used for receiving therapeutic substance from a filling syringe for at least partially filling the chamber and for connecting to a catheter assembly for dispensing therapeutic substance from the elastomeric bladder. Preferably, the elastomeric bladder has formed therein only a single port through the thickness thereof The single port is in fluid communication with the chamber and the bi-directional valve so that a user of the fluid reservoir will not be confused with multiple ports and which port to use for connection to the filling syringe and the catheter assembly.

In an alternative form, the present invention is directed to an infusion system which includes a fluid reservoir described above, as well as a catheter assembly. The catheter assembly includes a conduit and a catheter connector connected to the conduit and coupleable to the bidirectional valve of the fluid reservoir. The catheter assembly may also include a fluid flow restrictor and a filter. Both the fluid flow restrictor and the filter are preferably situated in the catheter assembly, as opposed to the fluid reservoir, so as not to restrict fluid flow into the elastomeric bladder through the bi-directional valve in order to fill the chamber of the elastomeric bladder.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 2 is an exploded isometric view of a portion of the pressurized fluid reservoir of the present invention shown in FIG. 1.

DETAILED DESCRIPTION OF THE PREFERRED EMBODIMENTS

Figure 1:
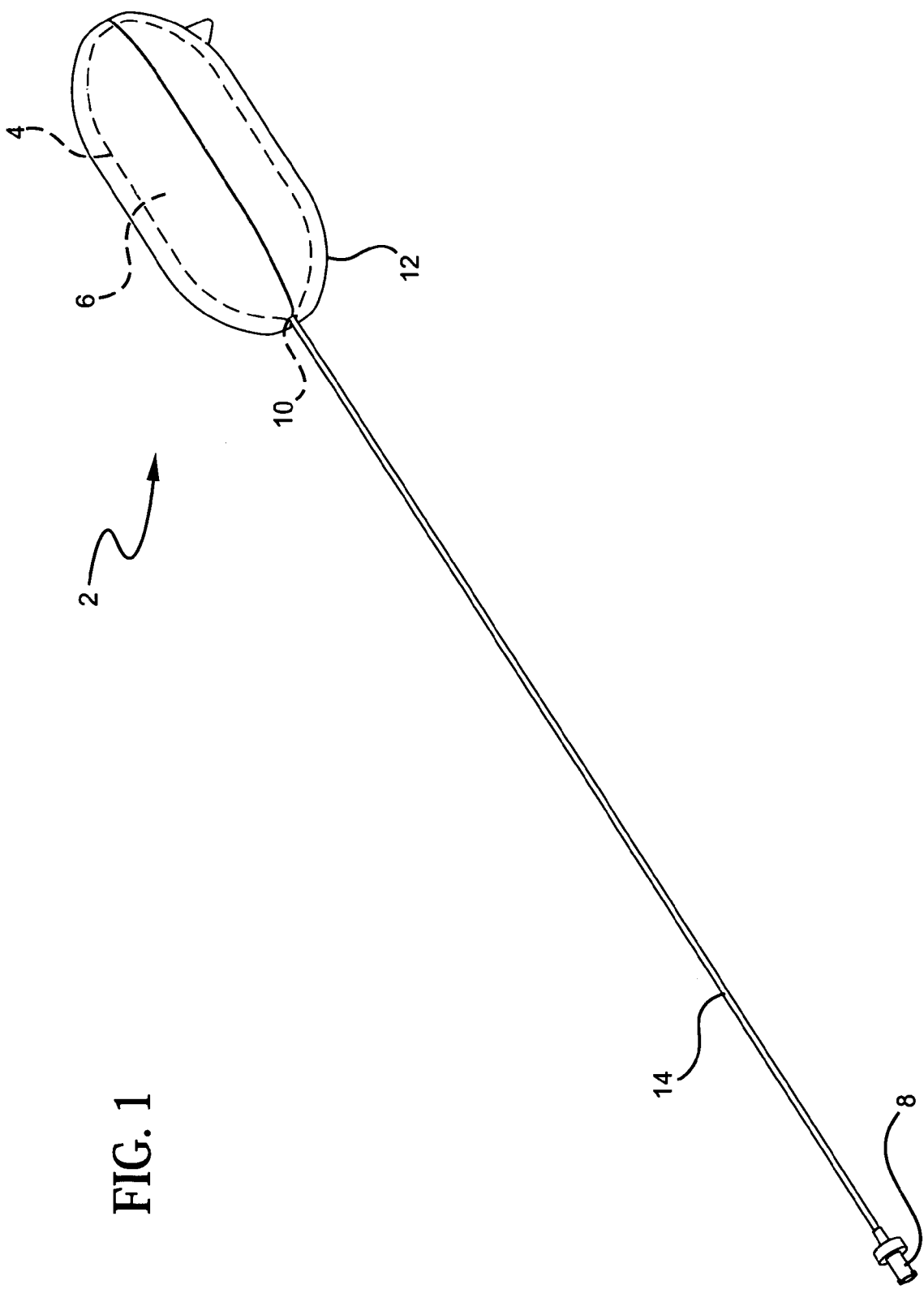
FIG. 1 is a perspective view of one form of a pressurized fluid reservoir for an infusion system formed in accordance with one form of the present invention.

Initially referring to FIGS. 1 and 2 of the drawings, it will be seen that a fluid reservoir 2 for use with a medical infusion system includes an elastomeric bladder 4 which is expandable and contractable and which defines a chamber 6 therein for receiving and containing a volume of therapeutic substance, such as a therapeutic liquid, gas, oxygen, or a combination of a liquid and a gas, and exerting pressure on the substance contained therein to force the therapeutic substance from the bladder 4 in order to dispense the therapeutic substance through a catheter assembly to a patient undergoing treatment. The fluid reservoir 2 further includes a bi-directional valve 8 which is in fluid communication with the chamber 6 of the elastomeric bladder 4. The bi-directional valve 8 is provided for receiving therapeutic substance for at least partially filling the chamber 6 of the elastomeric bladder 4 and for dispensing therapeutic substance therefrom to a patient.

Preferably, the elastomeric bladder 4 has formed therein a single port 10 through the thickness thereof, which port 10 is in fluid communication with the chamber 6 and the bi-directional valve 8. Preferably, no other port is provided on the elastomeric bladder 4 or, for that matter, the fluid reservoir 2 of the present invention, so as to avoid confusion to the user (e.g., healthcare provider) as to which port should be used for connecting to a syringe or similar device for filling the reservoir or connecting to a catheter assembly for dispensing therapeutic fluid from the reservoir. The elastomeric bladder 4 of the fluid reservoir is filled by connecting the filling syringe to the same bi-directional valve 8 which is used to connect to a catheter assembly for dispensing the therapeutic substance from the filled elastomeric bladder, which greatly simplifies the fluid reservoir's use.

Preferably, and as shown in FIGS. 1 and 2 of the drawings, the fluid reservoir 2 includes a protective housing 12 which defines an interior space in which the elastomeric bladder 4 is situated. A conduit 14 in the form of a flexible, medical grade tubing, is coupled to the elastomeric bladder 4 and the bi-directional valve 8 and defines a fluid passageway which is in communication with the bi-directional valve 8 and the single port 10 and chamber 6 of the elastomeric bladder. Preferably, the protective housing 12 is formed with a first section 16 and a second section 18 which mates with the first section 16 so that the elastomeric bladder 4 may be placed within the interior space defined by the housing 12 prior to the assembly of the first and second sections 16, 18 of the housing.

A preferred form of a portion of the fluid reservoir 2 of the first embodiment of the present invention is shown in the exploded view of FIG. 2. There, it will be seen that the expandable elastomeric bladder 4 is preferably in the form of a cylindrical tube 20 having a first open axial end 22 and a second open axial end 24 opposite the first open axial end 22. A first adaptor 26 is at least partially received by the first open axial end 22 of the elastomeric bladder 4. The first adaptor 26 has an outer surface and a recess 28 formed circumferentially about the outer surface. The first adaptor 26 has a bore 30 extending axially therethrough, which bore 30 is in fluid communication with the chamber 6 of the elastomeric bladder 4. As will be seen, the first adaptor 26 defines the single port 10 of the elastomeric bladder 4. The first adaptor 26 preferably includes a male plug 32 which extends axially outwardly therefrom through which the bore 30 extends. The plug 32 is used for connection to an end of the flexible conduit 14 of the fluid reservoir 2.

A second adaptor 34 is at least partially received by the second open axial end 24 of the elastomeric bladder 4. The second adaptor 34 has an outer surface and a recess 36 formed circumferentially about its outer surface. The second adaptor 34 provides a fluidtight seal and effectively closes the second open axial end 24 of the elastomeric bladder 4.

A first o-ring 38 is received by the recess 28 formed in the first adaptor 26 and engages a portion of the elastomeric bladder 4 at the first open axial end 22. More specifically, the first axial end 22 of the elastomeric bladder extends over the recess 28 in the first adaptor 26 and is held captive therein by the compressive force of the resilient first o-ring 38. Preferably, the end portion of the first open axial end 22 of the elastomeric bladder 4 is then folded over the first o-ring 38 upon and in contact with itself and forms a fluidtight seal with the first adaptor 26. Then, a first end cap 40 having a circumferential wall of a predetermined radius is snap-fitted over the rolled-over portion of the first axial end 22 of the elastomeric bladder to encapsulate and secure the elastomeric bladder 4 to the first adaptor 26. The first end cap 40 has an opening 42 formed through the thickness thereof which at least partially receives therethrough the male plug 32 of the first adaptor 26 so that the male plug 32 extends beyond the outer exposed surface of the first end cap 40 and is connectable to one end of the fluid conduit 14.

A second o-ring 44 is similarly received by the recess 36 formed in the second adaptor 34 and compressibly engages a portion of the elastomeric bladder 4 at the second open axial end 24 of the bladder 4 and holds the second axial end 24 in place partially within the recess 36 by the resiliency and compressive force of the second o-ring 44. As with the first axial end, the end of the second axial end 24 of the elastomeric bladder 4 is folded over the second o-ring 44 upon and in contact with itself to further secure it to the second adaptor 34 and provide a fluidtight seal therewith. A second end cap 46, also having a circumferentially extending wall 48 of a predetermined radius, is snap-fitted onto the rolled-over end of the second axial end 24 of the elastomeric bladder to encapsulate and secure the second end to the second adaptor 34, in much the same way as with the first end cap 40. Preferably, no opening or bore is formed through the second end cap 46 or the second adaptor 34 so that the second axial end 24 of the elastomeric bladder 4 is sealed against fluid leakage.

Hemispherical cutouts 50 may be formed in the mating first and second sections 16, 18 of the housing 12 or in interior transverse walls 51 of the housing sections to receive and capture the first and second end caps 40, 46 when the housing sections 16, 18 are assembled together. In this manner, a fully encased, expandable elastomeric bladder 4 having a single port for receiving and dispensing a therapeutic fluid and connectable to the conduit 14 which, in turn, is connected to the bi-directional valve 8, is provided.

The elastomeric bladder 4 of the present invention, such as that shown in FIGS. 1 and 2 of the drawings, preferably has a wall with a thickness of about 0.063 inches, to provide the required expansion and contraction, and concomitant pressure exerted on the therapeutic substance contained therein to expel the therapeutic substance with enough force to deliver the same to a patient undergoing treatment. The elastomeric bladder 4 also has a preferred axial length of about 3.5 inches, a preferred outer diameter of about 0.130 inches and a preferred inner diameter of about 0.080 inches. Such dimensions will provide an elastomeric bladder with a capacity to hold about 300 milliliters of a therapeutic substance. Of course, it is envisioned to be within the scope of the present invention to provide an elastomeric bladder with other dimensions than those described above in order to hold and dispense greater or lesser volumes of a therapeutic substance. Optimal bladder characteristics will also depend on the desired flow rate for the complete infusion system, which flow rate is determined by a) the pressure supplied by the reservoir and b) the resistance to flow provided by the geometry of the flow restrictor.

Preferably, the elastomeric bladder 4 is formed of a medical grade, low durometer, silicone material, preferably having a hardness of about 30 Shore A durometer. Even more specifically, the elastomeric bladder is preferably formed from a material known as MED-4025 manufactured by NuSil Technology, LLC of Carpinteria, Calif. This preferred material (i.e., MED-4025) is a silicone elastomer which has an elongation of about 900 percent, a tensile strength of about 1600 pounds per square inch, a hardness of about 30 Shore A durometer and a tear resistance of about 140 pounds per inch, although other silicone elastometers varying greatly in the aforementioned characteristics may be suitable for use in forming the bladder 4 and are envisioned to be within the scope of the present invention. Preferably, silicone is used as the material for its elastomeric properties, and because silicone tends to adhere to itself over time, which further helps secure the folded-over axial ends 22, 24 of the elastomeric bladder upon itself and increases the robustness of the preferred design and prevents the o-rings 38, 44 and bladder 4 from becoming displaced relative to each other, either by the o-rings rolling or through bladder creepage. This further allows a bladder 4 having a thinner wall to be used, which minimizes the force required to fill the bladder with the therapeutic substance, making it easier to use by a healthcare provider than conventional thick-walled bladders. Although an elastomeric bladder 4 is preferably formed from a silicone material, other elastomers and materials may be used, such as a polymer or synthetic rubber or a latex material. Furthermore, the elastomeric bladder 4 may be formed from a single tubular member or a plurality of co-axially arranged tubular members joined end-to-end by intermediary fluidtight connectors or couplers, for example, or the like.

As described previously, preferably a bi-directional valve 8 is used on the fluid reservoir 2 to both fill the chamber 6 of the elastomeric bladder by coupling the valve to a filling syringe and to dispense the therapeutic substance contained in the bladder chamber 6 by connecting the valve 8 to a catheter assembly or a tubing set, preferably one designed to deliver therapeutic agents into the body of a medical patient, for example, that disclosed in U.S. Pat. No. 5,419,770 which issued to Richard E. Crass et al., the disclosure of which is incorporated herein by reference. The bi-directional valve 8 is preferably a two-way luer-lock reflux valve, such as the Safsite™ needle-free value having Part No. S5401010S manufactured by B. Braun Medical Inc. of Bethlehem, Pa. Of course, other bi-directional valves may be suitable for use and are considered to be within the scope of the present invention.

The bi-directional valve 8 serves as the input and output mechanism for fluid transport. A standard male tipped luer-lock syringe may be mated with the bi-directional valve 8 such that the valve automatically opens and the contents of the syringe may be transferred to the reservoir of the present invention. The syringe may then be removed, thereby causing the bi-directional valve 8 to automatically close. This procedure may be repeated to fill the reservoir 2 with a therapeutic substance to the desired or maximum volume. At this point, the reservoir may be connected to a tubing set or catheter assembly, as described previously, wherein the connector device on the tubing set or catheter assembly is a male-tipped luer fitting. Flow from the pressurized elastomeric bladder 4 of the reservoir 2 automatically commences through the tubing set or catheter assembly. It should be noted that luer mechanisms do not need to be used to provide this functionality, as any mating valve and connector components may be used. Luer fittings are preferably used because of their general acceptance in the medical field and for their compatibility with needle free devices, such as syringes.

As mentioned previously, and as shown in FIGS. 1 and 2, the bi-directional valve 8 is in fluid communication with the chamber 6 of the elastomeric bladder 4 through the flexible medical grade tubing 14 connecting the valve with the bladder.

Figure 3:
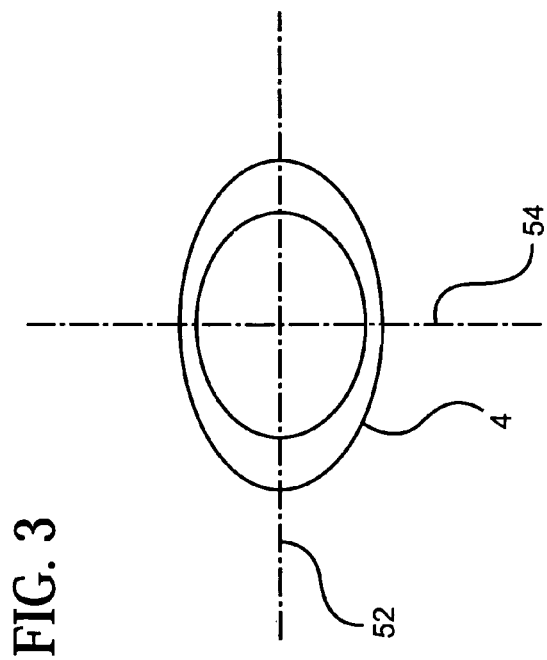
FIG. 3 is a transverse cross-sectional view of a portion of a pressurized fluid reservoir for an infusion system formed in accordance with a second form of the present invention.
Figure 5:
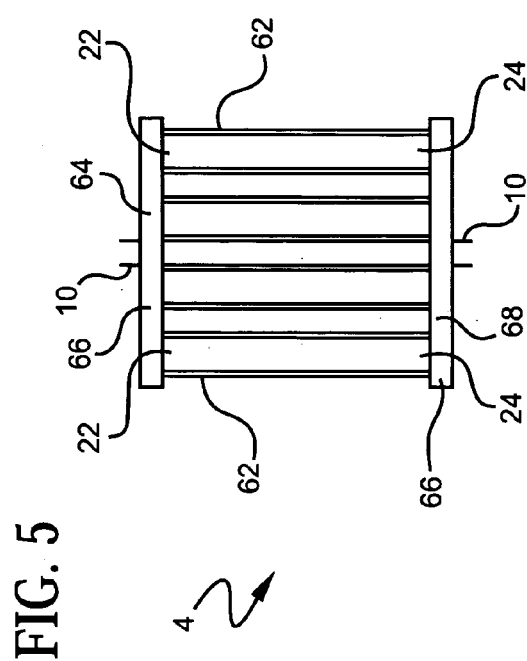
FIG. 5 is a cross-sectional view of a pressurized fluid reservoir for an infusion system formed in accordance with a fourth embodiment of the present invention.

In a second embodiment of the present invention, as shown in FIG. 3 of the drawings, a low-profile or pocket-sized fluid reservoir 2 is provided. More specifically, the elastomeric bladder 4 of the reservoir 2 may be formed with a generally oblong shape in transverse cross-section. The bladder 4 may have a substantially consistent wall thickness about its transverse and/or longitudinal cross-section or, more preferably, may have different wall thicknesses over selected portions thereof to allow for greater or lesser expansion in one direction or another.

Even more specifically, the generally oblong shape of the elastomeric bladder 4 in transverse cross-section may be described as where the bladder has a first width situated along a transverse major axis 52 and a second width situated along a transverse minor axis 54 which is disposed perpendicularly to the transverse major axis 52, where the first width is greater than the second width. Preferably, the bladder 4 includes a continuous wall surrounding the first and second widths thereof. The continuous wall has a first thickness at the first width of the elastomeric bladder, and a second thickness at the second width of the bladder. The first thickness is greater than the second thickness in order to allow the elastomeric bladder 4 to expand along the transverse major axis 52 more than its expansion along the transverse minor axis 54. Thus, the same volume of a therapeutic substance may be contained in an oblong-shaped bladder, such as shown in FIG. 3, as in a cylindrically-shaped bladder, such as shown in FIG. 2, and yet the oblong-shaped bladder 4 will provide the fluid reservoir 2 of the present invention with a low profile so that it is wearable by a patient undergoing treatment, or with the ability to be carried in the patient's pocket, which increases the mobility of the patient undergoing treatment.

Figure 4:
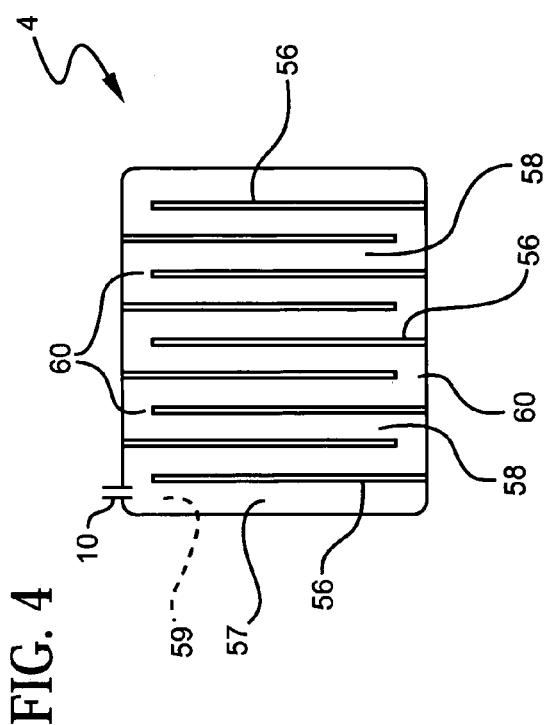
FIG. 4 is a cross-sectional view of a portion of a pressurized fluid reservoir for an infusion system formed in accordance with a third embodiment of the present invention.

In yet a third embodiment of the present invention, and as shown in FIG. 4 of the drawings, the elastomeric bladder 4 of the fluid reservoir 2 may be formed with structure similar to that of the common air mattress. More specifically, the elastomeric bladder 4 includes front and rear outer walls 57, 59 which are preferably generally parallel to each other, and a plurality of walls 56 or other structure, such as welds or seams, which joint the front and rear outer walls 57, 59 together at predetermined spaced apart locations along the width of the front and rear outer walls. More specifically, the walls 56 or other structure are spaced apart from each other and are co-parallelly arranged in a side-by-side relationship within the interior chamber 6 of the elastomeric bladder 4. The walls 56 or other structure define a series of adjacent fluid channels 58, where the adjacent fluid channels 58 are in fluid communication with each other through breaks or openings 60 in the dividing walls 56 or other structure. This structure provides the fluid reservoir 2 of the present invention with a low profile and with controlled expansion and contraction of the elastomeric bladder 4. Again, preferably a single port 10 formed in the elastomeric bladder 4 is in fluid communication with the bidirectional valve 8 through the flexible tubing 14 so that the bladder chamber 6 and the fluid channels 58 thereof may be filled with a therapeutic substance and from which the therapeutic substance may be dispensed to the patient undergoing treatment.

In a fourth embodiment of the present invention, the fluid reservoir 2 of the present invention may include an elastomeric bladder 4 formed from a plurality of expandable elongated tubes 62, such as the cylindrical tube 20 shown in FIG. 2 of the drawings. Each expandable elongated tube 62 has a first open axial end 22 and a second open axial end 24 opposite the first open axial end 22. The tubes 62 are arranged co-parallelly in a side-by-side relationship. A first manifold 64 defining an internal passageway 66 is connected to the first open axial end 22 of each of the expandable elongated tubes 62. Similarly, a second manifold 68, also defining an interior passageway 66, is connected to the second open axial end 24 of each of the expandable elongated tubes 62. The passageways 66 of the first and second manifolds 64, 68 are in fluid communication with the elongated tubes 62, and at least the first manifold passageway 66 is in fluid communication with the bidirectional valve 8, although it is envisioned that the passageways of both manifolds 64, 68 may fluidly communicate with the valve. Alternatively, a solid piece that maintains alignment of the tubes 62 but that does not allow fluid passage may be substituted for the second manifold 68. Again, this particular design of the fluid reservoir 2 provides the fluid reservoir with a low profile and compact shape so that it is not so obtrusive and so that it may be worn or carried by a patient undergoing treatment.

Figure 6:
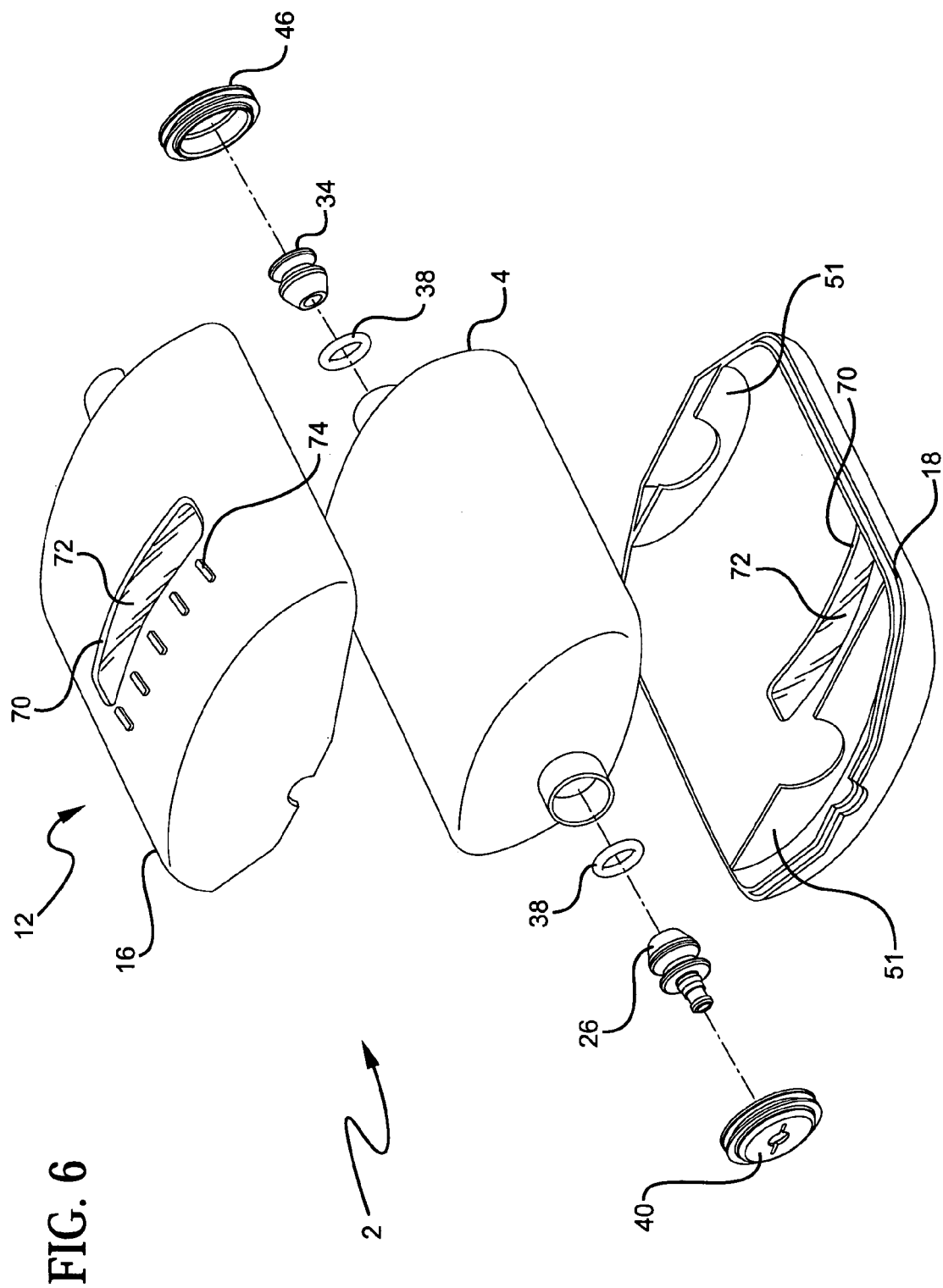
FIG. 6 is an exploded isometric view of a portion of a pressurized fluid reservoir for an infusion system formed in accordance with a fifth embodiment of the present invention.

FIG. 6 illustrates a fifth embodiment of the fluid reservoir 2 of the present invention. In this particular embodiment, the protective housing 12 which covers the elastomeric bladder 4, especially an elastomeric bladder that is oblong in transverse cross-sectional shape and which can expand to a greater extent in a sideways direction, such as shown in FIG. 3, preferably includes a window 70 for viewing the elastomeric bladder 4. The window 70 may be defined by an opening or cutout formed through the thickness of the housing 12, in one or more mating sections 16, 18 of the housing, with or without a transparent covering or plastic insert 72 situated over or in the cutout. In proximity to the window 70 and imprinted on the housing 12, or formed in the exposed surface thereof, are a plurality of markings or gradations 74 preferably situated across the width of the window 70. The window 70 and the markings or gradations 74 situated at the window are provided to allow the user to view and sense the relative expansion or contraction of the elastomeric bladder 4 either when the bladder chamber 6 is being filled with a therapeutic substance, or when a therapeutic substance is being dispensed by the fluid reservoir 2 of the present invention.

As mentioned previously, the pressurized fluid reservoir 2 of the present invention is connectable to a catheter assembly 76 which is meant generically herein to include the conventional tubing set disclosed in the aforementioned U.S. Pat. No. 5,419,770 to Crass et al. Together, the fluid reservoir 2 and the catheter assembly 76 form an infusion system for providing a therapeutic substance to a patient undergoing treatment, and such an infusion system is envisioned to form part of, and be within the scope of, the present invention.

Figure 7:
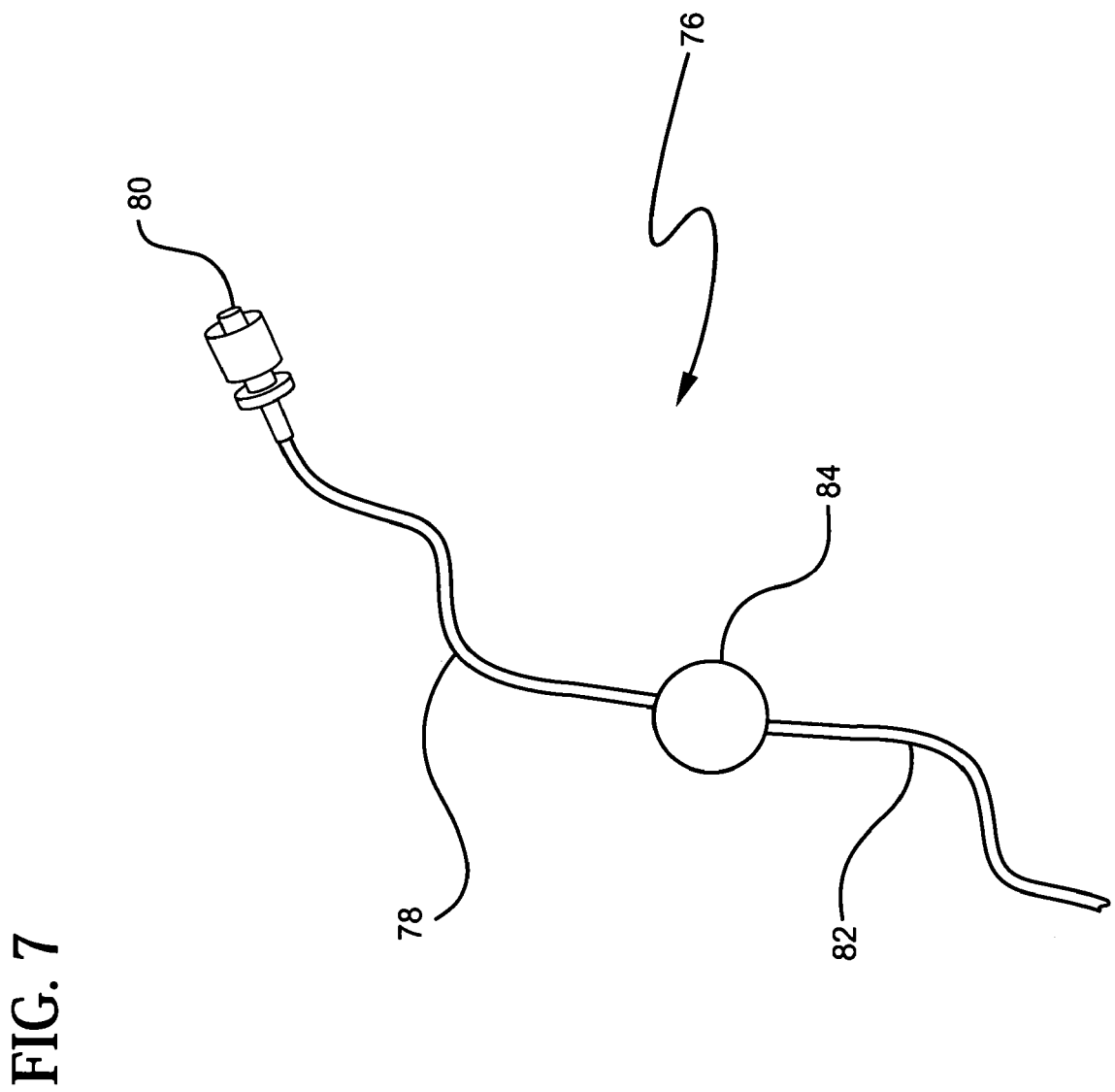
FIG. 7 is a perspective view of a catheter assembly forming part of an infusion system formed in accordance with the present invention.

More specifically, the catheter assembly 76 of the present invention, as shown in FIG. 7 of the drawings, includes a flexible medical tubing or conduit 78, and a catheter connector 80 connected to the tubing 78 and coupleable to the bidirectional valve 8 of the fluid reservoir 2. The catheter connector 80 is preferably a male-tipped luer fitting which automatically opens the bi-directional valve 8 when coupled thereto. Preferably, the catheter assembly 76 includes a fluid flow restrictor 82 which is in fluid communication with the conduit 78 of the catheter assembly. The fluid flow restrictor 82 may be tubing having a selected inner diameter or may be another device which regulates the flow of therapeutic substance from the pressurized reservoir 2 through the catheter tubing 78 to the patient. The catheter assembly 76 may further include an in-line filter 84 which is in fluid communication with the conduit or tubing 78 of the catheter assembly. Here, it should be noted that the filter 84 and the fluid flow restrictor 82 are preferably not situated in, or forming part of, the fluid reservoir 2 of the present invention, but rather are forming part of the catheter assembly 76 which is selectively connected to the bi-directional valve 8 of the fluid reservoir 2. In this way, neither the fluid flow restrictor 82 nor the filter 84 will impede the ability of the fluid reservoir 2 to be filled with a therapeutic substance through the single, bi-directional valve 8 connected to the elastomeric bladder 4.

The advantages of the fluid reservoir 2 and infusion system of the present invention over conventional reservoirs and infusion systems are many. The particular design of the present invention mitigates some of the risks inherent in the designs in the prior art. Firstly, the bi-directional valve 8 serves as the only connection device. The devices in the prior art that contain connectors that may be mated with needle-free devices utilize two connectors, such as disclosed in the aforementioned U.S. Pat. No. 5,080,652 to Sancoff et al., or utilize a stop-cock such as disclosed in the aforementioned U.S. Pat. No. 4,909,790 to Tsujakawa et al. The devices that utilize two connectors cannot allow bi-directional flow because these devices incorporate mechanisms that are uni-directional, such as filters. This results in increased confusion for the user, an increase in human factor misuse risk, and the potential for damaging the device, for example, by damaging the filter. Such is avoided with the present invention by having a single port in the form of a bi-directional valve 8 for both filling the elastomeric bladder 4 of the fluid reservoir 2 and dispensing a therapeutic substance therefrom, all through the same single bi-directional valve 8.

Furthermore, the design of the present invention mitigates the risk associated with existing elastomeric infusion pump devices wherein the filling process is conducive to compromising the device's structure or dropping it on the floor. Existing infusion pump reservoirs having elastomeric bladders require connecting the filling syringe directly to the input port of the device. In this manner, the conventional infusion device must be balanced atop the syringe while it is being filled. Because a significant amount of force is required to perform this filling step, users of these devices have reported that the devices have slipped while they were being filled. This could ruin the connector, may result in the device being dropped on the floor, may result in knocking other medical implements to the floor, or may even injure the user or patient. The design of the present invention, on the other hand, removes the need for balancing the reservoir device atop the syringe, and eliminates the need for a separate tubing set, thereby mitigating some of the difficulty of filling the reservoir. Furthermore, the fluid reservoir 2 of the present invention is designed to minimize the loading force that the user must apply by having a relatively thin elastomeric bladder 4, thereby further reducing the potential for these risks.

The design of the fluid reservoir 2 of the present invention also discourages the accidental or inadvertent connection of unrelated medical devices. The frequency of this problem has been rising in recent years, as needle-free devices have become more prevalent. The fluid inlet of most medical devices is a female luer fitting, while the fluid outlet of most medical devices is a male luer fitting. Because the bi-directional valve 8 of the fluid reservoir 2 of the present invention serves as both the fluid inlet and fluid outlet, and because the bi-directional valve requires a male luer fitting to activate the flow, and further because there is only one connector device, the number of unrelated devices that could be mated with the fluid reservoir of the present invention is significantly reduced.

Additionally, existing infusion pump devices regulate commencement and termination of flow using either a clamp or a stop-cock. Often, a patient inadvertently ceases the delivery of a therapeutic fluid from the infusion device by accidentally closing the clamp, for example, by sitting on it. As a result, some surgeons and nurses have begun the practice of removing the clamp from the infusion device. But, because the clamps are not designed to be removed, this action could potentially harm the infusion device, such as by cutting the device's tubing. The use of a bi-directional valve 8 in the fluid reservoir 2 of the present invention negates the need for a clamp or a stop-cock and thereby removes any potentiality of the patient inadvertently ceasing the flow by the inadvertent manipulation of a clamp or stop-cock or similar device. Furthermore, this means that there is no clamp for a surgeon to consider removing.

Also, by providing an elastomeric bladder 4 having a non-circular transverse cross-section or with a variable wall thickness, a low profile or pocket-sized fluid reservoir 2 may be realized, so that the fluid reservoir may be worn or carried more comfortably and in a more concealed manner (as compared to existing ambulatory infusion systems) by the patient undergoing treatment which increases his or her mobility.

The fluid reservoir 2 of the present invention may be designed to enable mid-use manipulation outside of the hospital by a non-medical professional in a sterile and safe manner. In particular, pre-filled reservoirs may be provided to the patient in order to enable the patient to replace a depleted or expired reservoir with a full reservoir in order to extend the duration of the infusion therapy. While current infusion devices are difficult to manipulate, that is, fluid commencement is not automatic and tubing clamps are frequently misused, the use of the bi-directional valve 8 of the fluid reservoir 2 of the present invention greatly facilitates the manipulation of the fluid reservoir compared to conventional infusion pumps. It follows, then, that pre-filled reservoirs may be provided to a patient to allow him or her to replace a depleted or expired reservoir in order to extend the duration of infusion therapy provided by the fluid reservoir of the present invention. Because the flow commences automatically into the tubing set or catheter assembly 76 when the plunger of the bi-directional valve 8 is depressed, there is no need for manipulation of a tubing clamp. Furthermore, a sterilization grade filter 84 may be placed in the tubing set or catheter assembly 76, rather than in the fluid reservoir 2 of the present invention, so that the connector 80 of the tubing set or catheter assembly mates with the bi-directional valve 8 of the fluid reservoir to enable and maintain sterility of the infused fluid.

It should be further noted that the fluid reservoir 2 of the present invention may be used for enhancing the oxygen concentration in tissues of patients, especially in healing wounds. The syringe may transfer both air and/or fluid into the reservoir 2, or the reservoir may be partially filled to provide an open volume containing air. As an alternative to air, oxygen gas may be added to the reservoir through the two-way valve 8 in addition to the therapeutic fluid. As the fluid reservoir 2 is filled, the internal pressure inside the bladder chamber 6 becomes greater than the external ambient pressure and, as a consequence, the solubility of gasses in the fluid, including oxygen, also increases. Consequently, the fluid that is delivered to the patient through a catheter connected to the fluid reservoir 2 is enriched in oxygen, which enhances the healing process at the wound site. By combining an oxygen rich gas with the therapeutic fluid, a two-fold benefit may be provided by a single pump: 1) the benefit provided from the therapeutic fluid (e.g., anesthesia, antibiotic benefit, etc.) and 2) the benefit derived from the presence of the oxygen.

In this regard, and as previously mentioned, the fluid reservoir 2 of the present invention may be filled by using a syringe, but other methods of filling and pressuring the elastomeric bladder 4 of the fluid reservoir may be suitable for use. For example, a small canister of compressed oxygen gas may be affixed to the bi-directional valve 8 after pre-filling the bladder chamber with fluid. Alternatively, oxygen pressure lines continuously used in a hospital setting may be affixed to the bi-directional valve 8 of the fluid reservoir. The fluids used in the reservoir may be aqueous in nature, or may be of a type that has a high affinity of oxygen and enables a high oxygen solubility, such as fluorocarbon liquid. Oxygenated fluids enhance wound healing and also reduce the likelihood of infection.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A fluid reservoir for an infusion system, which comprises:
    an expandable elastomeric bladder defining a chamber for receiving and containing a volume of therapeutic substance and exerting pressure thereon;
    a bi-directional valve in fluid communication with the chamber of the elastomeric bladder for receiving therapeutic substance for at least partially filling the chamber and for dispensing therapeutic substance therefrom; and
    a flexible conduit extending between the elastomeric bladder and the bi-directional valve and defining a fluid passageway which is in fluid communication with the bi-directional valve and the chamber of the elastomeric bladder.

2. A fluid reservoir for an infusion system as defined by claim 1, wherein the elastomeric bladder has formed therein a single port through the thickness thereof, the single port being in fluid communication with the chamber, the flexible conduit, and the bi-directional valve.

3. A fluid reservoir for an infusion system as defined by claim 2, wherein the bi-directional valve includes a two-way luer check valve, the two-way luer check valve opening upon attachment of a filling syringe having a male luer end for receiving therapeutic substance from the syringe to at least partially fill the elastomeric bladder, and opening upon attachment to a catheter assembly having a catheter connector for dispensing therapeutic substance contained in the elastomeric bladder to the catheter assembly.

4. A fluid reservoir for an infusion system as defined by claim 2, wherein the flexible conduit comprises a flexible tube coupled to the elastomeric bladder and the bi-directional valve and defining a fluid passageway which is in fluid communication with the bi-directional valve, the single port and the chamber of the elastomeric bladder.

5. A fluid reservoir for an infusion system as defined by claim 1, wherein the elastomeric bladder includes a wall having a thickness of about 0.063 inches.

6. A fluid reservoir for an infusion system as defined by claim 5, wherein the elastomeric bladder has a length of about 3.5 inches.

7. A fluid reservoir for an infusion system as defined by claim 1, wherein the elastomeric bladder is formed of a medical grade silicone material having a hardness of about 30 Shore A durometer.

8. A fluid reservoir for an infusion system as defined by claim 1, wherein the elastomeric bladder is formed from a silicone elastomer having an elongation of about 900 percent, a tensile strength of about 1600 pounds per square inch, a hardness of about 30 Shore A durometer and a tear resistance of about 140 pounds per inch.

9. A fluid reservoir for an infusion system as defined by claim 1, wherein the elastomeric bladder is formed of a polymer rubber or latex material.

10. A fluid reservoir for an infusion system as defined by claim 2, which further comprises:
    a protective housing, the protective housing defining an interior space in which the elastomeric bladder is situated, the elastomeric bladder being in the form of a cylindrical tube having a first open axial end and a second open axial end opposite the first open axial end;
    a first adaptor being at least partially received by the first open axial end of the elastomeric bladder, the first adaptor having an outer surface and a recess formed circumferentially about the outer surface thereof, the first adaptor having a bore extending axially therethrough and being in fluid communication with the chamber of the elastomeric bladder, the first adaptor defining the single port of the elastomeric bladder;
    a second adaptor being at least partially received by the second open axial end of the elastomeric bladder, the second adaptor having an outer surface and a recess formed circumferentially about the outer surface thereof, the second adaptor providing a fluidtight seal and effectively closing the second open axial end of the elastomeric bladder; and
    first and second o-rings, the first o-ring being received by the recess formed in the first adaptor and engaging a portion of the elastomeric bladder at the first open axial end thereof, the second o-ring being received by the recess formed in the second adaptor and engaging a portion of the elastomeric bladder at the second open axial end thereof.

11. A fluid reservoir for an infusion system as defined by claim 10, which further comprises:
    a first end cap, the first end cap being mounted on the protective housing, the first end cap having an opening formed through the thickness thereof, the first adaptor having a male plug extending through the first end cap opening for connection to the flexible conduit; and
    a second end cap, the second end cap being mounted on the protective housing, the second end cap covering at least a portion of the second adaptor.

12. A fluid reservoir for an infusion system as defined by claim 1, wherein the elastomeric bladder is formed with a generally oblong shape in transverse cross-section and having a first width situated along a major axis and a second width situated along a minor axis disposed perpendicularly to the major axis, the first width being greater than the second width.

13. A fluid reservoir for an infusion system as defined by claim 12, wherein the elastomeric bladder includes a continuous wall surrounding the first and second widths thereof, the continuous wall having a first thickness at the first width of the elastomeric bladder, and a second thickness at the second width of the elastomeric bladder, the first thickness being greater than the second thickness to allow the elastomeric bladder to expand along the major axis greater than along the minor axis.

14. A fluid reservoir for an infusion system as defined by claim 1, wherein the elastomeric bladder includes a plurality of joining members, the joining members being spaced apart from one another and being co-parallelly arranged in a side-by-side relationship within the interior chamber of the elastomeric bladder, the joining members defining a series of adjacent fluid channels, the adjacent fluid channels being in fluid communication with each other.

15. A fluid reservoir for an infusion system as defined by claim 1, wherein the elastomeric bladder includes a plurality of expandable elongated tubes, each expandable elongated tube having at least a first open axial end, the tubes being arranged co-parallelly in a side-by-side relationship, and at least one manifold, the manifold being connected to the first open axial end of each of the expandable elongated tubes, the manifold defining a passageway which is in fluid communication with the expandable elongated tubes, the manifold being in fluid communication with the bi-directional valve.

16. A fluid reservoir for an infusion system as defined by claim 1, wherein the bi-directional valve includes a two-way luer check valve, the two-way luer check valve opening upon attachment of a filling syringe having a male luer end for receiving therapeutic substance from the syringe to at least partially fill the elastomeric bladder, and opening upon attachment to a catheter assembly having a catheter connector for dispensing therapeutic substance contained in the elastomeric bladder to the catheter assembly.

17. A fluid reservoir for an infusion system as defined by claim 1, which further comprises:
a protective housing, the protective housing defining an interior space in which the elastomeric bladder is situated, the flexible conduit having a first end adjacent the protective housing and a second end spaced from the protective housing, wherein the bi-directional valve is connected to the second end of the flexible conduit for spacing the bi-directional valve from the protective housing.

18. A fluid reservoir for an infusion system as defined by claim 1, wherein the therapeutic substance received by the chamber of the elastomeric bladder includes at least one of a gas and a liquid.

19. An infusion system, which comprises:
a fluid reservoir, the fluid reservoir including an expandable elastomeric bladder defining a chamber for receiving and containing a volume of therapeutic substance and exerting pressure thereon, a bidirectional valve in fluid communication with the chamber of the elastomeric bladder for receiving therapeutic substance for at least partially filling the chamber and for dispensing therapeutic substance therefrom, the elastomeric bladder having formed therein a single port through the thickness thereof, the single port being in fluid communication with the chamber and the bidirectional valve; a flexible tube extending between the single port and the bidirectional valve; and
a catheter assembly, the catheter assembly including a conduit, and a catheter connector connected to the conduit and coupleable to the bidirectional valve of the fluid reservoir.

20. An infusion system as defined by claim 19, wherein the flexible tube spaces the bidirectional valve from the single port, and wherein the bidirectional valve includes a two-way luer check valve, the two-way luer check valve opening upon attachment of a filling syringe having a male luer end for receiving therapeutic substance from the syringe to at least partially fill the elastomeric bladder, and opening upon attachment to a catheter assembly having a catheter connector for dispensing therapeutic substance contained in the elastomeric bladder to the catheter assembly.

21. An infusion system as defined by claim 19, wherein the catheter assembly further includes a fluid flow restrictor in fluid communication with the conduit of the catheter assembly.

22. An infusion system as defined by claim 19, wherein the catheter assembly further includes a filter, the filter being in fluid communication with the conduit of the catheter assembly.

23. A method of delivering a therapeutic substance to a patient, which comprises the steps of:
filling a fluid reservoir through a bidirectional valve of the fluid reservoir with a therapeutic substance, the fluid reservoir including an expandable elastomeric bladder defining a chamber for receiving and containing a volume of the therapeutic substance and exerting pressure thereon, the bidirectional valve being in fluid communication with the chamber of the elastomeric bladder for receiving the therapeutic substance for at least partially filling the chamber and for dispensing therapeutic substance therefrom, the elastomeric bladder having formed therein a single port through the thickness thereof, the single port being in fluid communication with the chamber and the bidirectional valve, wherein the bidirectional valve is coupled with the single port of the elastomeric bladder via a flexible tube;
connecting a catheter assembly to the fluid reservoir, the catheter assembly including a conduit and a catheter connector connected to the conduit and coupleable to the bidirectional valve of the fluid reservoir, the catheter assembly and fluid reservoir connected thereto being fluid communicateable with a patient; and
dispensing therapeutic substance from the chamber of the elastomeric bladder of the fluid reservoir and through the catheter assembly to a patient.

24. A method of delivering a therapeutic substance to a patient as defined by claim 23, wherein the therapeutic substance received by the chamber of the elastomeric bladder and delivered to a patient includes at least one of a gas and a liquid.

25. A fluid reservoir for an infusion system as defined by claim 1, which further comprises:
a protective housing defining an interior space in which the elastomeric bladder is situated, wherein the flexible conduit projects from the protective housing for spacing the bi-directional valve from the protective housing.

26. A method of delivering a therapeutic substance to a patient as defined by claim 23, wherein the flexible tube spaces the bidirectional valve from the single port of the elastomeric bladder.

* * * * *